US008304212B2

(12) United States Patent
Baez-Vasquez et al.

(10) Patent No.: US 8,304,212 B2
(45) Date of Patent: Nov. 6, 2012

(54) METHODS AND COMPOSITIONS FOR DEGRADATION OF LIGNOCELLULOSIC MATERIAL

(75) Inventors: Marco A. Baez-Vasquez, Jupiter, FL (US); Richard Burlingame, Jupiter, FL (US); Jon K. Magnuson, Richland, WA (US); Marion Bradford, Hendersonville, NC (US); Arkady Panteleimonovich Sinitsyn, Moscow (RU)

(73) Assignees: Dyadic International, Inc., Jupiter, FL (US); Battelle Memorial Institute, Richland, WA (US); Iowa Corn Promotion Board, Johnston, IA (US)

( * ) Notice: Subject to any disclaimer, the term of this patent is extended or adjusted under 35 U.S.C. 154(b) by 0 days.

(21) Appl. No.: 11/775,777

(22) Filed: Jul. 10, 2007

(65) Prior Publication Data

US 2008/0076159 A1  Mar. 27, 2008

Related U.S. Application Data

(60) Provisional application No. 60/806,876, filed on Jul. 10, 2006.

(51) Int. Cl.
*C12P 19/00* (2006.01)
*C12N 9/00* (2006.01)
*C12N 9/14* (2006.01)
*C12N 1/00* (2006.01)

(52) U.S. Cl. .......... 435/72; 435/183; 435/195; 435/243; 435/254.1

(58) Field of Classification Search .................. None
See application file for complete search history.

(56) References Cited

U.S. PATENT DOCUMENTS

| | | | |
|---|---|---|---|
| 4,326,032 | A | 4/1982 | Grove |
| 4,478,854 | A | 10/1984 | Adler-Nissen et al. |
| 4,478,939 | A | 10/1984 | Adler-Nissen et al. |
| 4,840,903 | A | 6/1989 | Wu |
| 4,940,838 | A | 7/1990 | Schilperoort et al. |
| 5,464,763 | A | 11/1995 | Schilperoort et al. |
| 5,789,227 | A | 8/1998 | Dees |
| 6,258,175 | B1 | 7/2001 | Lightner |
| 6,573,086 | B1 | 6/2003 | Emalfrab et al. |
| 6,667,066 | B2 | 12/2003 | Labeille et al. |
| 7,049,485 | B2 | 5/2006 | Sticklen et al. |
| 7,067,303 | B1 | 6/2006 | Nichols et al. |
| 2003/0109011 | A1 | 6/2003 | Hood et al. |
| 2004/0005674 | A1 | 1/2004 | Duck et al. |
| 2006/0057251 | A1 | 3/2006 | Dawley et al. |
| 2006/0110812 | A1 | 5/2006 | O'Neal Ingram et al. |

OTHER PUBLICATIONS

Krogh et al. Appl Biochem Biotechnol. 2004 Spring;113-116:389-401.*
Fagerstrom et al. Biotechnol Appl Biochem. Apr. 1995;21 ( Pt 2):223-31 (ABSTRACT).*
Margolles-Clark et al. Appl Environ Microbiol. Oct. 1996;62(10):3840-6.*
Barnett et al. Biotechnology (N Y). Jun. 1991;9(6):562-7 (ABSTRACT).*
Altschul, et al, "Gapped BLAST and PSI-BLAST: A new generation of protein database search programs", Nucleic Acid Res., Sep. 1, 1997, vol. 25, No. 17, pp. 3389-3402.
Chou, et al., "Prediction of the secondary structure of proteins from their amino acid sequence", Advances in enzymology and related areas of molecular biology, 1978, vol. 47, pp. 45-148.
Christou, et al., "Stable transformation of soybean by electroporation and root formation from transformed callus", Proceedings of the National Academy of Sciences of the United States of America, Jun. 1987, vol. 84, No. 12, pp. 3962-3966.
D'Halluin, et al., "Transgenic maize plants by tissue electroporation", The Plant Cell, Dec. 1992, vol. 4, No. 12, pp. 1495-1505.
Deshayes, et al., "Liposome-mediated transformation of tobacco mesophyll protoplasts by an *Escherichia coli* plasmid", Nov. 1985, The EMBO Journal, vol. 4, No. 11, pp. 2731-2737.
Draper, et al., "Ti Plasmid Homologous Sequences Present in Tissues from *Agrobacterium* Plasmid-transformed *Petunia* Protoplasts", Plant and Cell Physiology, 1982, vol. 23, pp. 451-458.
Gruber, et al., "Vectors for Plant Transformation", Methods in Plant Molecular Biology and Biotechnology, 1993, pp. 89-119.
Hain, et al., "Uptake, integration, expression and genetic transmission of a selectable chimaeric gene by plant protoplasts", Molecular and General Genetics MGG, 1985, vol. 199, pp. 161-168.
Horsch, et al., "A Simple and general method for Transferring Genes into Plants" Science, Mar. 8, 1985, vol. 227, pp. 1229-1231.
Hsu, "Pretreatment of Biomass", Handbook on Bioethanol: Production and Utilization, pp. 179-212, 1996.
Kado, et al., "Molecular Mechanisms of Crown Gall Tumorigenesis", Critical Reviews in Plant Sciences, 1991, vol. 10, No. 1, pp. 1-32.
Katahira, et al., "Ethanol fermentation from lignocelulosic hydrolysate by a recombinant xylose-and cellooligosaccharide-assimilating yeast strain", Applied Microbiology and Biotechnology, Oct. 2006, pp. 1136-1143, vol. 72.
Klein, et al., "Transformation of Microbes, Plants and Animals by Particle Bombardment", Bio/Technology, Mar. 1992, vol. 10, pp. 286-291.
Kyte, et al., "A simple method for displaying the hydropathic character of a protein", Journal of Molecular Biology, May 5, 1992, vol. 157, No. 1, pp. 105-132.
Moloney, et al., "High efficiency transformation of *Brassica napus* using *Agrobacterium* vectors", Plant Cell Reports, 1989, vol. 8, pp. 238-242.
Miki, et al., "Procedures for Introducing Foreign DNA into Plants", Methods in Plant Molecular Biology and Biotechnology, 1993, pp. 67-88.
Sanford, et al., "Delivery of Substances into Cells and Tissues Using a Particle Bombardment Process", Particulate Science and Technology, 5:27-37 (1987).

(Continued)

Primary Examiner — Christian Fronda
(74) Attorney, Agent, or Firm — Michael J. Keller; Roetzel & Andress (57) ABSTRACT

Methods to convert lignocellulosic biomass to fermentable sugars with enzymes that degrade the lignocellulosic material are provided, as well as novel combinations of enzymes, including those that provide a synergistic release of sugars from plant biomass.

7 Claims, 3 Drawing Sheets

OTHER PUBLICATIONS

Sanford, et al., "The Biolistic Process", Trends in Biotech., Dec. 1988, vol. 6, pp. 299-302.

Sanford, "Biolistic plant transformation", Physiologia Plantarum, 1990, vol. 79, pp. 206-209.

Laursen, et al., "Production of fertile transgenic maize by electroporation of suspension culture cells", Plant molecular biology, Jan. 1994, vol. 24, No. 1, pp. 51-61.

Stemmer, "DNA shuffling by random fragmentation and reassembly: in vitro recombination for molecular evolution", Proceedings of the National Academy of Sciences of the United States of America, Oct. 25, 1994, vol. 91, No. 22, pp. 10747-10751.

Tatusova, et al, "Blast 2 Sequences—a new tool for comparing protein and nucleotide sequences", FEMS Microbiology Letters, May 15, 1999, vol. 174, No. 2, pp. 247-250.

Wyman, et al., "Coordinated development of leading biomass", Bioresource Technology, Dec. 2005, vol. 96, No. 18, pp. 1959-1966.

Wyman, et al., "Comparative sugar recovery data from laboratory scale application of leading pretreatment technologies to corn stove", Bioresource Technology, Dec. 2005, vol. 96, No. 18, pp. 2026-2032.

Zhang, et al., "Efficient transformation of tobacco by ultrasonication", Bio/Technology, 1991, vol. 9, pp. 996-997.

International Search Report for International (PCT) Patent Application No. PCT/US07/73180, mailed Aug. 5, 2008.

Written Opinion for International (PCT) Patent Application No. PCT/US07/73180, mailed Aug. 5, 2008.

Mosier, et al., "Features of promising technologies for pretreatment of lignocellulosic biomass", Bioresource Technology, Apr. 2005, vol. 96, No. 6, pp. 673-686.

International Preliminary Report on Patentability for International (PCT) Patent Application No. PCT/US07/73180, issued Jan. 13, 2009.

\* cited by examiner

METHODS AND COMPOSITIONS FOR DEGRADATION OF LIGNOCELLULOSIC MATERIAL

CROSS-REFERENCE TO RELATED APPLICATIONS

This application claims the benefit of priority under 35 U.S.C. §119(e) of U.S. Provisional Application No. 60/806,876, filed on Jul. 10, 2006, the entire disclosure of which is incorporated herein by reference.

FIELD OF THE INVENTION

The invention relates to a method to convert lignocellulosic biomass to fermentable sugars with enzymes that degrade the lignocellulosic material. The invention also relates to novel combinations of enzymes, including those that provide a synergistic release of sugars from plant biomass.

BACKGROUND OF THE INVENTION

Large amounts of carbohydrates in plant biomass provide a plentiful source of potential energy in the form of sugars (both five carbon and six carbon sugars) that could be utilized for numerous industrial and agricultural processes. However, the enormous energy potential of these carbohydrates is currently under-utilized because the sugars are locked in complex polymers, and hence are not readily accessible for fermentation. These complex polymers are often referred to collectively as lignocellulose. Sugars generated from degradation of plant biomass could provide plentiful, economically competitive feedstocks for fermentation into chemicals, plastics, and fuels, including ethanol as a substitute for petroleum.

For example, distillers' dried grains (DDG) are lignocellulosic byproducts of the corn dry milling process. Milled whole corn kernels are treated with amylases to liquefy the starch within the kernels and hydrolyze it to glucose. The glucose so produced is then fermented in a second step to ethanol. The residual solids after the ethanol fermentation and distillation are centrifuged and dried, and the resulting product is DDG, which is used as an animal feed stock. Although DDG composition can vary, a typical composition for DDG is: 32% hemicellulose, 22% cellulose, 30% protein, 10% lipids, 4% residual starch, and 4% inorganics. In theory, the cellulose and hemicellulose fractions, comprising about 54% of the weight of the DDG, can be efficiently hydrolyzed to fermentable sugars by enzymes; however, it has been found that the carbohydrates comprising lignocellulosic materials in DDG are more difficult to digest. To date, the efficiency of hydrolysis of these (hemi) cellulosic polymers by enzymes is much lower than the hydrolytic efficiency of starch, due to the more complex and recalcitrant nature of these substrates. Accordingly, the cost of producing the requisite enzymes is higher than the cost of producing amylases for starch hydrolysis. It is therefore desirable to produce inexpensive enzyme mixtures that efficiently degrade cellulose and hemicellulose.

SUMMARY OF THE INVENTION

One embodiment of the present invention provides a multi-enzyme product comprising a product of a *Chrysosporium* including *Chrysosporium lucknowense* and exhibiting a glucoamylase activity of at least about 0.05 U per milligram of dry matter, a 0-glucosidase activity of at least about 22 nmol/min/mg of dry matter, and an α-arabinofuranosidase activity of at least about 9 nmol/min/mg of dry matter In some embodiments, the *Chrysosporium lucknowense* is selected from the group consisting of Strain C1 (Accession No. VKM F-3500-D); Strain UV13-6 (Accession No. VKM F-3632 D); Strain NG7C-19 (Accession No. VKM F-3633 D); and/or Strain UV18-25 (Accession No. VKM F-3631 D) and mutants or derivatives thereof.

The present invention also provides a multi-enzyme product comprising a product of a *Trichoderma* including *Trichoderma reesei* and exhibiting a glucoamylase activity of at least about 0.001 U per milligram of dry matter, a β-xylosidase activity of at least about 280 nmol/min/mg of dry matter, a β-glucosidase activity of at least about 454 nmol/min/mg of dry matter, and an α-arabinofuranosidase activity of at least about 100 nmol/min/mg of dry matter.

The present invention also provides a multi-enzyme product comprising a product of a *Aspergillus* including *Aspergillus japonicus* and exhibiting a glucoamylase activity of at least about 0.65 U per milligram of dry matter, a β-xylosidase activity of at least about 553 nmol/min/mg of dry matter, a β-glucosidase activity of at least about 167 nmol/min/mg of dry matter, and an α-arabinofuranosidase activity of at least about 62 nmol/min/mg of dry matter.

The present invention also provides a multi-enzyme product comprising a product of a *Penicillium* including *Penicillium funiculosum* (*Talaromyces* including *Talaromyces flavus*) and exhibiting a glucoamylase activity of at least about 0.18 U per milligram of dry matter, a xylosidase activity of at least about 8 nmol/min/mg of dry matter, a β-glucosidase activity of at least about 691 nmol/min/mg of dry matter, and an α-arabinofuranosidase activity of at least about 29 nmol/min/mg of dry matter.

The present invention also provides a multi-enzyme product comprising a product of a *Penicillium* including *Penicillium canescens* (*P. solitum*) and exhibiting a glucoamylase activity of at least about 0.08 U per milligram of dry matter, a β-xylosidase activity of at least about 15 nmol/min/mg of dry matter, a β-glucosidase activity of at least about 40 nmol/min/mg of dry matter, and an α-arabinofuranosidase activity of at least about 956 nmol/min/mg of dry matter.

In some embodiments, any of the above-described multi-enzyme products is a crude fermentation product.

In some embodiments, any of the above-described multi-enzyme products has been subjected to a purification step.

The present invention further provides a method for degrading a lignocellulosic material to fermentable sugars, comprising contacting the lignocellulosic material with an effective amount of a multi-enzyme product derived from one microorganism, whereby at least one fermentable sugar is produced, and wherein the multi-enzyme product comprises at least one enzyme in the multi-enzyme products of the present invention.

In some embodiments, at least one enzyme in the multi-enzyme product is derived from *Trichoderma* including *Trichoderma reesei*, *Chrysosporium* including *Chrysosporium lucknowense*, *Aspergillus* including *Aspergillus japonicus*, *Penicillium* including *Penicillium canescens* or *solitum*, *Penicillium* including *Penicillium funiculosum* (*Talaromyces* including *Talaromyces flavus*), or mutants of any of the foregoing.

In some embodiments, the lignocellulosic material is selected from the group consisting of herbaceous material, agricultural residue, forestry residue, municipal solid waste, waste paper, and pulp and paper mill residue.

In some embodiments, the lignocellulosic material is distiller's dried grains or distiller's dried grains with solubles. In some embodiments, the distiller's dried grains or distiller's dried grains with solubles are derived from corn.

In some embodiments, the multi-enzyme product comprises at least one hemicellulase. In some embodiments, the hemicellulase is selected from the group consisting of a xylanase, and arabinofuranosidase, an acetyl xylan esterase, a glucuronidase, an endo-galactanase, a mannanase, an endo-arabinase, an exo-arabinase, an exo-galactanase, a ferulic acid esterase, a galactomannanase, a xylogluconase, and mixtures thereof.

In some embodiments, the xylanase is selected from the group consisting of endoxylanases, exoxylanase, and β-xylosidase.

In some embodiments, the multi-enzyme product comprises at least one cellulase.

In some embodiments, the multi-enzyme product comprises at least two multi-enzyme products of the present invention.

In some embodiments, the method for degrading a lignocellulosic material to fermentable sugars further comprises treating the lignocellulosic material with an effective amount of one or more accessory enzymes. In some embodiments, the accessory enzyme is a glucoamylase, a pectinase, or a ligninase.

In some embodiments, the accessory enzyme is added as a crude or a semi-purified enzyme mixture.

In some embodiments, the accessory enzyme is produced by culturing at least one organism on a substrate to produce the enzyme.

In some embodiments, the method for degrading a lignocellulosic material to fermentable sugars further comprises a pretreatment process. In some embodiments, the pretreatment process is physical treatment, metal ion, ultraviolet light, ozone, organosolv treatment, steam explosion treatment, lime impregnation with steam explosion treatment, hydrogen peroxide treatment, hydrogen peroxide/ozone (peroxone) treatment, acid treatment, dilute acid treatment, base treatment, heat treatment or AFEX.

In some embodiments, the heat treatment comprises heating the lignocellulosic material to at least about 121° C. for at least about 15 minutes.

In some embodiments, the method for degrading a lignocellulosic material to fermentable sugars further comprises detoxifying the lignocellulosic material.

In some embodiments, the method for degrading a lignocellulosic material to fermentable sugars further comprises recovering the fermentable sugar. In some embodiments, the sugar is glucose, xylose, arabinose, galactose, mannose, rhamnose, sucrose or fructose.

In some embodiments, the method for degrading a lignocellulosic material to fermentable sugars further comprises recovering the residual lignocellulosic material after degrading the lignocellulosic material to fermentable sugars.

The present invention also provides a method for degrading distiller's dried grains or distiller's dried grains with solubles to sugars, the method comprising contacting the distiller's dried grains or distiller's dried grains with solubles with a multi-enzyme product obtained from the fermentation of at least one microorganism, whereby at least 10% of the fermentable sugars are liberated, wherein at least one enzyme in the multi-enzyme product comprises at least one of the enzymes in the multi-enzyme products of the present invention.

In some embodiments, at least 15%, at least 20%, or at least 23% of the sugars are liberated.

In some embodiments, the distiller's dried grains or distiller's dried grains with solubles are derived from corn.

In some embodiments, the multi-enzyme product comprises at least one hemicellulase. The hemicellulase may be a xylanase, an arabinofuranosidase, an acetyl xylan esterase, a glucuronidase, an endo-galactanase, a mannanase, an endo-arabinase, an exo-arabinase, an exo-galactanase, a ferulic acid esterase, a galactomannanase, a xyloglucanase, or mixtures thereof. In some embodiments, the xylanase is an endoxylanase, exoxylanase, or β-xylosidase.

In some embodiments, the multi-enzyme product comprises at least one cellulase.

In some embodiments, the multi-enzyme product comprises at least two multi-enzyme products of the present invention.

In some embodiments, the method for degrading distiller's dried grains or distiller's dried grains with solubles to sugars further comprises treating distiller's dried grains or distiller's dried grains with solubles with an effective amount of one or more accessory enzymes. In some embodiments, the accessory enzyme is a glucoamylase, a pectinase, or a ligninase.

In some embodiments, the accessory enzyme is added as a crude or a semi-purified enzyme mixture.

In some embodiments, the accessory enzyme is produced by culturing at least one organism on a substrate to produce the enzyme.

In some embodiments, the method for degrading distiller's dried grains or distiller's dried grains with solubles to sugars further comprises a pretreatment process. In some embodiments, the pretreatment process is physical treatment, metal ion, ultraviolet light, ozone, organosolv treatment, steam explosion treatment, lime impregnation with steam explosion treatment, hydrogen peroxide treatment, hydrogen peroxide/ozone (peroxone) treatment, acid treatment, dilute acid treatment, base treatment, heat treatment or AFEX.

In some embodiments, the heat treatment comprises heating the distiller's dried grains or distiller's dried grains with solubles to at least about 121° C. for at least about 15 minutes.

In some embodiments, the method for degrading distiller's dried grains or distiller's dried grains with solubles to sugars further comprises detoxifying the distiller's dried grains or distiller's dried grains with solubles.

In some embodiments, the method for degrading distiller's dried grains or distiller's dried grains with solubles to sugars further comprises recovering the fermentable sugar. In some embodiments, the sugar is glucose, xylose, arabinose, galactose or mannose.

In some embodiments, the method for degrading distiller's dried grains or distiller's dried grains with solubles to sugars further comprises recovering the residual distiller's dried grains or distiller's dried grains with solubles after degrading the distiller's dried grains or distiller's dried grains with solubles to fermentable sugars.

The present invention further provides a method for producing an organic substance comprising saccharifying a lignocellulosic material with an effective amount of a multi-enzyme product obtained from at least one microorganism, wherein at least one enzyme in the multi-enzyme product comprises at least one of the enzymes in the multi-enzyme products of the present invention; fermenting the saccharified lignocellulosic material obtained with one or more fermenting microorganisms; and recovering the organic substance from the fermentation.

In some embodiments, the lignocellulosic material is herbaceous material, agricultural residue, forestry residue, municipal solid waste, waste paper, or pulp and paper mill residue. In some embodiments, the lignocellulosic material is distiller's dried grains or distiller's dried grains with solubles. The distiller's dried grains or distiller's dried grains with solubles can be derived from corn.

In some embodiments, the multi-enzyme product comprises at least one hemicellulase. In some embodiments, the hemicellulase is a xylanase, an arabinofuranosidase, an acetyl xylan esterase, a glucuronidase, an endo-galactanase, a mannanase, an endo-arabinase, an exo-arabinase, an exo-galactanase, a ferulic acid esterase, a galactomannanase, a xylogluconase, or mixtures thereof. In some embodiments, the xylanase is an endoxylanase, exoxylanase, or xylosidase.

In some embodiments, the multi-enzyme product comprises at least one cellulase.

In some embodiments, the method for producing an organic substance further comprises treating the lignocellulosic material with an effective amount of one or more accessory enzymes.

In some embodiments, the accessory enzyme is a glucoamylase, a pectinase, or a ligninase.

In some embodiments, the accessory enzyme is added as a crude or a semi-purified enzyme mixture.

In some embodiments, the accessory enzyme is produced by culturing at least one organism on a substrate to produce the enzyme.

In some embodiments, the method for producing an organic substance further comprises a pretreatment process. In some embodiments, the pretreatment process is physical treatment, metal ion, ultraviolet light, ozone, organosolv treatment, steam explosion treatment, lime impregnation with steam explosion treatment, hydrogen peroxide treatment, hydrogen peroxide/ozone (peroxone) treatment, acid treatment, dilute acid treatment, base treatment, heat treatment or AFEX.

In some embodiments, the heat treatment comprises heating the lignocellulosic material to at least about 121° C. for at least about 15 minutes.

In some embodiments, the method for producing an organic substance further comprises detoxifying the lignocellulosic material.

In some embodiments, the steps are performed simultaneously in a simultaneous saccharification and fermentation.

In some embodiments, the organic substance is an alcohol, organic acid, ketone, amino acid, or gas. In some embodiments, the alcohol is ethanol.

The present invention also provides a method for producing a multi-enzyme product capable of producing fermentable sugars comprising cultivating a microorganism selected from the group consisting of *Trichoderma* including *Trichoderma reesei*, *Chrysosporium* including *Chrysosporium lucknowense*, *Aspergillus* including *Aspergillus japonicus*, *Penicillium* including *Penicillium canescens* or *solitum*, *Penicillium* including *Penicillium funiculosum* (*Talaromyces* including *Talaromyces flavus*) and mutants thereof in a nutrient medium, and recovering the multi-enzyme product from the fermentation broth.

The present invention further provides a method for producing fermentable sugars comprising cultivating a microorganism selected from the group consisting of *Trichoderma* including *Trichoderma reesei*, *Chrysosporium* including *Chrysosporium lucknowense*, *Aspergillus* including *Aspergillus japonicus*, *Penicillium* including *Penicillium canescens* or *solitum*, *Penicillium* including *Penicillium funiculosum* (*Talaromyces* including *Talaromyces flavus*) and mutants thereof in a nutrient medium comprising a lignocellulosic material, whereby fermentable sugars are produced.

In some embodiments, the lignocellulosic material is herbaceous material, agricultural residue, forestry residue, municipal solid waste, waste paper, or pulp and paper mill residue. In some embodiments, the lignocellulosic material is distiller's dried grains or distiller's dried grains with solubles.

In some embodiments, the distiller's dried grains or distiller's dried grains with solubles are derived from corn.

In some embodiments, the nutrient medium further comprises one or more accessory enzymes. In some embodiments, the accessory enzyme is a glucoamylase, a pectinase, or a ligninase.

In some embodiments, the accessory enzyme is added as a crude or a semi-purified enzyme mixture.

In some embodiments, the nutrient medium further comprises an agent for detoxifying the lignocellulosic material.

In some embodiments, the method for producing fermentable sugars further comprises recovering the fermentable sugar. In some embodiments, the sugar is glucose, xylose, mannose, galactose, or arabinose.

The present invention also provides a genetically modified organism comprising components suitable for degrading a lignocellulosic material to fermentable sugars, wherein the organism has been genetically modified to overexpress at least one enzyme of the multi-enzyme products of the present invention.

In some embodiments, the genetically modified organism is a microorganism. In some embodiments, the microorganism is a filamentous fungus. In some embodiments, the filamentous fungus is *Trichoderma* including *Trichoderma reesei*, *Chrysosporium* including *Chrysosporium lucknowense*, *Aspergillus* including *Aspergillus japonicus*, *Penicillium* including *Penicillium canescens* or *solitum*, or *Penicillium* including *Penicillium funiculosum* (*Talaromyces* including *Talaromyces flavus*).

In some embodiments, the genetically modified organism has been genetically modified to overexpress at least one accessory enzyme.

In some embodiments, the genetically modified organism is a plant.

The present invention also provides a recombinant enzyme isolated from a genetically modified microorganism of the present invention.

In some embodiments, the enzyme is part of a crude fermentation product.

In some embodiments, the recombinant enzyme has been subjected to a purification step.

The present invention also provides a recombinant enzyme derived from an enzyme of a multi-enzyme products of the present invention.

The present invention also provides a method for degrading a lignocellulosic material to fermentable sugars comprising contacting the lignocellulosic material with an effective amount of a multi-enzyme product derived from a genetically modified microorganism of the present invention, whereby at least one fermentable sugar is produced.

The present invention also provides a feed additive comprising a lignocellulosic material recovered from a method of the present invention. In some embodiments, the protein content of the recovered lignocellulosic material is higher than that of the starting lignocellulosic material.

The present invention further provides a method of improving the performance of an animal comprising administering to the animal a feed additive of the present invention.

The present invention also provides a method for improving the nutritional quality of an animal feed comprising adding a feed additive of the present invention to the animal feed.

The present invention further provides a genetically modified organism comprising components suitable for degrading a lignocellulosic material to fermentable sugars, wherein the microorganism is *Trichoderma reesei*, *Chrysosporium lucknowense*, *Aspergillus japonicus*, *Penicillium canescens*, or *Penicillium funiculosum*, and wherein the organism has been genetically modified to overexpress at least one enzyme in a multi-enzyme product of the present invention and at least one additional enzyme selected from the group consisting of a cellulase, a hemicellulase, a glucoamylase, a pectinase, and a ligninase.

DETAILED DESCRIPTION OF THE INVENTION

The present invention provides methods and compositions for the conversion of plant biomass to fermentable sugars that can be converted to useful products. The methods include methods for degrading lignocellulosic material using enzyme mixtures to liberate sugars. The compositions of the invention include enzyme combinations that break down lignocellulose. As used herein the terms "biomass" or "lignocellulosic material" includes materials containing cellulose and/or hemicellulose. Generally, these materials also contain xylan, lignin, protein, and carbohydrates, such as starch and sugar. Lignocellulose is generally found, for example, in the stems, leaves, hulls, husks, and cobs of plants or leaves, branches, and wood of trees. The process of converting a complex carbohydrate (such as starch or cellulose) into fermentable sugars is also referred to herein as "saccharification." Fermentable sugars, as used herein, refers to simple sugars, such as monosaccharides, disaccharides, and trisaccharides. Examples of sugars include glucose, xylose, arabinose, galactose, mannose, rhamnose, sucrose and fructose.

Biomass can include virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane bagasse, corn, corn stover, corn kernel including fiber from kernels, products and by-products from milling of grains such as corn, rye, oat bran, wheat and barley (including wet milling and dry milling) as well as municipal solid waste, waste paper and yard waste. The biomass can also be or include, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and/or hard and soft woods (not including woods with deleterious materials). In addition, agricultural biomass can include organic waste materials generated from agricultural processes including farming and forestry activities, specifically including forestry wood waste. Agricultural biomass may be any of the aforestated singularly or in any combination or mixture thereof. Biomass can also include crops grown for use in energy production such as switchgrass, miscanthus, elephantgrass, bermudagrass, energycane, erianthus and the like. Biomass may also include seed coats, including oil seed coats from canola, sunflower or soybean sources.

Biomass high in starch, sugar, or protein such as corn, grains, fruits and vegetables are usually consumed as food. Conversely, biomass high in cellulose, hemicellulose and lignin are not readily digestible and are primarily utilized for wood and paper products, animal feed, fuel, or are typically disposed. Generally, the substrate is of high lignocellulose content, including distillers' dried grains corn stover, corn cobs, rice straw, hay, sugarcane bagasse, and other agricultural biomass, switchgrass, forestry wastes, poplar wood chips, pine wood chips, sawdust, yard waste, and the like, including any combination of substrate.

In one embodiment, the lignocellulosic material is distillers' dried grains (DDG). DDG (also known as dried distiller's grain, or distiller's spent grain) is spent, dried grains recovered after alcohol fermentation. The lignocellulosic material can also be distiller's dried grain with soluble material recycled back (DDGS). While reference will be made herein to DDG for convenience and simplicity, it should be understood that both DDG and DDGS are contemplated as desired lignocellulosic materials. These are largely considered to be waste products and can be obtained after the fermentation of the starch derived from any of a number of grains, including corn, wheat, barley, oats, rice and rye. In one embodiment the DDG is derived from corn.

It should be noted that the distiller's grains do not necessarily have to be dried. Although the grains are normally, currently dried, water and enzymes are added to the DDG substrate in the present invention. If the saccharification were done on site, for example, the drying step could be eliminated and enzymes could be added to the distiller's grains without drying.

The present invention provides enzyme combinations that break down lignocellulose. Such enzyme combinations or mixtures can be multi-enzyme products from microorganisms, plants, or other organisms and synergistic enzyme mixtures comprising enzymes or multi-enzyme products from the microorganisms, plants or other organisms. Although reference to multi-enzyme products from microorganisms is typically made herein for simplicity, multi-enzyme products from plants or multi-enzyme products from combinations of organisms (e.g., microorganisms and plants or multiple microorganisms) are also contemplated. Synergistic enzyme combinations and related methods are contemplated. The invention includes methods to identify the optimum ratios and compositions of enzymes with which to degrade each lignocellulosic material. These methods entail tests to identify the optimum enzyme composition and ratios for efficient conversion of any lignocellulosic substrate to its constituent sugars. Such methods are described for DDG, for example, in Example 3.

The microorganisms useful in the present invention and/or as a source of enzymes useful in the present invention include any microorganism producing an enzyme capable of degrading lignocellulosic material, including bacteria, yeast, and filamentous fungi. For simplicity and convenience, filamentous fungal microorganisms will be discussed herein; however, one skilled in the art will recognize that other microorganisms will be useful in the present invention. Filamentous fungi have been widely used in industry for the production of proteins. These fungi are uniquely adapted for the production and secretion of proteins owing to their biological niche as microbial scavengers. In environments rich in biological polymers, such as forest floors, the fungi compete by secreting enzymes that degrade those polymers, producing monomers that can be readily utilized as nutrients for growth. The natural ability of fungi to produce proteins has been widely exploited, mainly for the production of industrial enzymes. Levels of protein production in natural isolates can be increased in improved strains by orders-of-magnitude and production yields of tens of grams of protein per liter of fermentation culture are commonplace. Fungal hosts, including, but not limited to, various species of *Talaromyces, Aspergillus, Trichoderma, Neurospora, Penicillium, Fusarium, Humicola, Myceliophthora, Corynascus, Chaetomium, Toypocladium, Thielavia, Acremonium, Sporotrichum, Thermoascus*, and *Chrysosporium*, are contemplated in the present invention. These are a few of many possible genera of fungi that will be useful sources of enzymes and/or would be suitable as host organisms for producing such enzymes mixtures. Such fungi can be obtained, for instance from various depositories such as the American Type Culture Collection (ATCC), the All Russian Collection of Microorganisms of the Russian Academy of Sciences (VKM), and Centraalbureau voor Schimmelcultures of the Royal Netherlands Academy of Arts and Sciences (CBS).

It should be noted that for some species of filamentous fungi, taxonomic placement can be difficult. Many studies of filamentous fungi are based on a morphological treatment, sequence data, sometimes from only one gene, usually rDNA ITS data. Other studies are polyphasic in nature and include other facets of fungal biology in a classification scheme. As a result, one isolate may be given one name in one classification scheme, and another name in a second classification scheme. Organisms referred to herein having names that may differ depending on the classification scheme are noted.

Once multi-enzyme products have been identified, novel enzymes with the ability to facilitate degradation of lignocellulosic material can be identified and isolated therefrom. Classical methods and modern molecular biology techniques can be utilized in this regard. For example, a set of genes believed to code for enzymes capable of degrading lignocellulosic can be identified. Recombinant techniques will also allow the construction of strains that contain mixtures of enzymes that are not normally found in nature by mixing and matching the genes for the corresponding enzymes. By testing combinations of naturally occurring or engineered enzymes from various sources for their ability to convert hemicellulosic substrates to fermentable sugars and applying the recombinant techniques to construct filamentous fungal or other microbial strains producing those mixtures of enzymes, it will be possible to produce economical mixtures of enzymes capable of the rapid degradation of cellulose and hemicellulosic substrates such as DDG in order to obtain higher value fuels or chemicals from these byproducts. One may generate such a pool of genes by searching databases for sequences of nucleic acids or amino acids with a given degree of sequence identity (similarity) to the gene or protein of interest (e.g., a *Penicillium funiculosum* β-xylosidase gene).

Degree of sequence identity refers to an evaluation of homology that is performed using a BLAST homology search. BLAST homology searches can be performed using the BLAST database and software, which offers search programs including: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schaaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
  Reward for match=1
  Penalty for mismatch=-2
  Open gap (5) and extension gap (2) penalties
  gap x_dropoff (50) expect (10) word size (11) filter (on)
For blastp, using 0 BLOSUM62 matrix:
  Open gap (11) and extension gap (1) penalties
  gap x_dropoff (50) expect (10) word size (3) filter (on).

In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching.

Searching can be done in any number of publicly available databases. For example, the MIPS *Neurospora crassa* Sequencing Project (description), the MIPS *Fusarium graminearum* Genome DataBase, the MIPS *Ustilago maydis* Genome DataBase, available at through the website for the Munich Information Center for Protein Sequences (MIPS), the DOE Joint Genome Institute (JGI) web site, the Fungal Genomics web site maintained by the Centre for Structural and Functional Genomics at Concordia University; and the Fungal Genome Initiative website maintained by the Broad Institute at the Massachusetts Institute of Technology.

Next, the desired set of genes can be cloned from libraries or amplified using methods known in the art, for example PCR (from strains containing these genes). Alternatively, one may design and synthesize the gene(s) by annealing and extending synthetic oligonucleotides. Methods for such gene synthesis are well known in the art. Subsequently, the resulting DNA is cloned into an expression vector in a manner such that the predicted proteins can be expressed in a host cell. Such a recombinant host cell or strain is also referred to herein as a genetically modified organism. A preferred recombinant host cell is a fungal cell. A preferred fungal expression system is described in U.S. Pat. No. 6,573,086, incorporated by reference herein in its entirety.

In further embodiments, methods are provided for evolving the polynucleotides and polypeptides of the present invention using molecular evolution techniques in an effort to create and identify novel variants with desired structural, functional, and/or physical characteristics. Molecular evolution techniques can be "DNA Shuffling", or "sexual PCR" (WPC, Stemmer, PNAS, 91:10747, (1994)), also referred to as "directed molecular evolution", "exon-shuffling", "directed enzyme evolution", "in vitro evolution", and "artificial evolution". Such reference terms are known in the art and are encompassed by the invention. Characterisitics such as activity, the protein's enzyme kinetics, the proteins $K_i$, $K_{cat}$, $K_m$, $V_{max}$, $K_d$, thermostability, pH optimum, and the like, can be modified. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

As used herein, a genetically modified microorganism can include a genetically modified bacterium, yeast, fungus, or other microbe. Such a genetically modified microorganism has a genome that is modified (i.e., mutated or changed) from its normal (i.e., wild-type or naturally occurring) form such that the desired result is achieved (i.e., increased or modified activity and/or production of at least one an enzyme or a multi-enzyme product for the conversion of lignocellulosic material to fermentable sugars). Genetic modification of a microorganism can be accomplished using classical strain development and/or molecular genetic techniques. Such techniques are known in the art and are generally disclosed for microorganisms, for example, in Sambrook et al., 1989, *Molecular Cloning: A Laboratory Manual*, Cold Spring Harbor Labs Press. The reference Sambrook et al., ibid., is incorporated by reference herein in its entirety. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

In one aspect of the invention, a genetically modified microorganism can endogenously contain and express an enzyme or a multi-enzyme product for the conversion of lignocellulosic material to fermentable sugars, and the genetic modification can be a genetic modification of one or more of such endogenous enzymes, whereby the modification has some effect on the ability of the microorganism to convert lignocellulosic material to fermentable sugars.

In another aspect of the invention, a genetically modified microorganism can endogenously contain and express an enzyme or a multi-enzyme product for the conversion of lignocellulosic material to fermentable sugars, and the genetic modification can be an introduction of at least one exogenous nucleic acid sequence (e.g., a recombinant nucleic acid molecule), wherein the exogenous nucleic acid sequence encodes at least one additional enzyme useful for the conversion of lignocellulosic material to fermentable sugars and/or a protein that improves the efficiency of the enzyme or multi-enzyme product for the conversion of lignocellulosic material to fermentable sugars. In this aspect of the invention, the microorganism can also have at least one modification to a gene or genes comprising its endogenous enzyme(s) for the conversion of lignocellulosic material to fermentable sugars.

In yet another aspect of the invention, the genetically modified microorganism does not necessarily endogenously (naturally) contain an enzyme or a multi-enzyme product for the conversion of lignocellulosic material to fermentable sugars, but is genetically modified to introduce at least one recombinant nucleic acid molecule encoding at least one enzyme, a multiplicity of enzymes, or a multi-enzyme product for the conversion of lignocellulosic material to fermentable sugars. Such a microorganism can be used in a method of the invention, or as a production microorganism for crude fermentation products, partially purified recombinant enzymes, and/or purified recombinant enzymes, any of which can then be used in a method of the present invention.

Once the proteins (enzymes) are expressed in a host cell, a cell extract that contains the activity to test can be generated. For example, a lysate from the host cell is produced, and the supernatant containing the activity is harvested and/or the activity can be isolated from the lysate. In the case of cells that secrete enzymes into the culture medium, the culture medium containing them can be harvested, and/or the activity can be purified from the culture medium. The extracts/activities prepared in this way can be tested using assays known in the art. Accordingly, methods to identify multi-enzyme products capable of degrading lignocellulosic biomass are provided (see Example 1 and 2).

Artificial substrates, or complex mixtures of polymeric carbohydrates and lignin, or actual lignocellulose can be used in such tests. One assay that may be used to measure the release of sugars and oligosaccharides from these complex substrates is the dinitrosalicylic acid assay (DNS) (see Example 1). In this assay, the lignocellulosic material such as DDG is incubated with enzymes(s) for various times and reducing sugars are measured.

The invention also contemplates genetically modified plants comprising such genes. The plants may be used for production of the enzymes, or as the lignocellulosic material used as a substrate in the methods of the invention. Methods to generate recombinant plants are known in the art. For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119.

The most widely utilized method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10:1 (1991). Descriptions of *Agrobacterium* vector systems and methods for *Agrobacterium*-mediated gene transfer are provided by numerous references, including Gruber et al., supra, Miki et al., supra, Moloney et al., *Plant Cell Reports* 8:238 (1989), and U.S. Pat. Nos. 4,940,838 and 5,464,763.

Another generally applicable method of plant transformation is microprojectile-mediated transformation wherein DNA is carried on the surface of microprojectiles. The expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992).

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p. 53 (1990); D'Halluin et al., *Plant Cell* 4:1495-1505 (1992) and Spencer et al., *Plant Mol. Biol.* 24:51-61 (1994).

As used herein, a multi-enzyme product can be obtained from or derived from a microbial, plant, or other source or combination thereof, and will contain enzymes capable of degrading lignocellulosic material. Examples of enzymes comprising the multi-enzyme products of the invention include, but are not limited to, cellulases, hemicellulases (such as xylanases, including endoxylanases, exoxylanase, and β-xylosidase), ligninases, amylases, glucuronidases, proteases, esterases (including ferulic acid esterase), lipases, glucosidases (such as glucosidase), glucomannanases, and xylogluconases.

In some embodiments, the multi-enzyme product comprises a hemicellulase. Hemicellulose is a complex polymer, and its composition often varies widely from organism to organism, and from one tissue type to another. In general, a main component of hemicellulose is beta-1,4-linked xylose, a five carbon sugar. However, this xylose is often branched as beta-1,3 linkages, and can be substituted with linkages to arabinose, galactose, mannose, glucuronic acid, or by esterification to acetic acid. Hemicellulose can also contain glucan, which is a general term for beta-linked six carbon sugars.

The composition, nature of substitution, and degree of branching of hemicellulose is very different in dicotyledonous plants (dicots, i.e., plant whose seeds have two cotyledons or seed leaves such as lima beans, peanuts, almonds, peas, kidney beans) as compared to monocotyledonous plants (monocots; i.e., plants having a single cotyledon or seed leaf such as corn, wheat, rice, grasses, barley). In dicots, hemicellulose is comprised mainly of xyloglucans that are 1,4-beta-linked glucose chains with 1,6-beta-linked xylosyl side chains. In monocots, including most grain crops, the principal components of hemicellulose are heteroxylans. These are primarily comprised of 1,4-beta-linked xylose backbone polymers with 1,3-beta linkages to arabinose, galactose and mannose as well as xylose modified by ester-linked acetic acids. Also present are branched beta glucans comprised of 1,3- and 1,4-beta-linked glucosyl chains. In monocots, cellulose, heteroxylans and beta glucans are present in roughly equal amounts, each comprising about 15-25% of the dry matter of cell walls. Hemicellulolytic enzymes, i.e., hemicellulases, include both exohydrolytic and endohydrolytic enzymes, such as xylanase, 1-xylosidase and esterases, which actively cleave hemicellulosic material through hydrolysis. Among these, xylanase and esterase enzymes cleave the xylan and acetyl side chains of xylan and the remaining xylo-oligomers are unsubstituted and can thus be hydrolyzed with β-xylosidase only. In addition, several less known side activities have been found in enzyme preparations that hydrolyze hemicellulose.

While the multi-enzyme product may contain many types of enzymes, mixtures comprising enzymes that increase or enhance sugar release from biomass are preferred, including hemicellulases. In one embodiment, the hemicellulase is a xylanase, an arabinofuranosidase, an acetyl xylan esterase, a glucuronidase, an endo-galactanase, a mannanase, an endo-arabinase, an exo-arabinase, an exo-galactanase, a ferulic acid esterase, a galactomannanase, a xylogluconase, or mixtures of any of these. In particular, the enzymes can include glucoamylase, β-xylosidase and/or β-glucosidase. The enzymes of the multi-enzyme product can be provided by a variety of sources. In one embodiment, the enzymes can be produced by a growing microorganisms or plants which produce the enzymes naturally or by virtue of being genetically modified to express the enzyme or enzymes. In another embodiment, at least one enzyme of the multi-enzyme product is commercially available.

One embodiment of the present invention relates to an isolated enzyme for catalyzing the conversion of lignocellulosic material to fermentable sugars as described herein, a homologue thereof, and/or a fragment thereof. Also included in the invention are isolated nucleic acid molecules encoding any of such proteins, homologues or fragments thereof. According to the present invention, an isolated protein or polypeptide is a protein that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. An isolated peptide can be produced synthetically (e.g., chemically, such as by peptide synthesis) or recombinantly. An isolated protein can also be provided as a crude fermentation product, or a protein preparation that has been partially purified or purified (e.g., from a microorganism) using protein purification procedures known in the art. In addition, and solely by way of example, a protein referenced as being derived from or from a particular organism, such as a "*Chrysosporium lucknowense* hemicellulase" refers to a hemicellulase (generally including a homologue of a naturally occurring hemicellulase) from a *Chrysosporium lucknowense* microorganism, or to a hemicellulase that has been otherwise produced from the knowledge of the structure (e.g., sequence), and perhaps the function, of a naturally occurring hemicellulase from *Chrysosporium lucknowense*. In other words, general reference to a *Chrysosporium lucknowense* hemicellulase or a hemicellulase derived from *Chrysosporium lucknowense* includes any hemicellulase that has substantially similar structure and function of a naturally occurring hemicellulase from *Chrysosporium lucknowense* or that is a biologically active (i.e., has biological activity) homologue of a naturally occurring hemicellulase from *Chrysosporium lucknowense* as described in detail herein. As such, a *Chrysosporium luckowense* hemicellulase can include purified, partially purified, recombinant, mutated/modified and synthetic proteins. The same description applies to reference to other proteins or peptides described herein and to other microbial sources for such proteins or peptides.

According to the present invention, the terms "modification" and "mutation" can be used interchangeably, particularly with regard to the modifications/mutations to the primary amino acid sequences of a protein or peptide (or nucleic acid sequences) described herein. The term "modification" can also be used to describe post-translational modifications to a protein or peptide including, but not limited to, methylation, farnesylation, carboxymethylation, geranyl geranylation, glycosylation, phosphorylation, acetylation, myristoylation, prenylation, palmitation, and/or amidation. Modifications can also include, for example, complexing a protein or peptide with another compound. Such modifications can be considered to be mutations, for example, if the modification is different than the post-translational modification that occurs in the natural, wild-type protein or peptide.

As used herein, the term "homologue" is used to refer to a protein or peptide which differs from a naturally occurring protein or peptide (i.e., the "prototype" or "wild-type" protein) by one or more minor modifications or mutations to the naturally occurring protein or peptide, but which maintains the overall basic protein and side chain structure of the naturally occurring form (i.e., such that the homologue is identifiable as being related to the wild-type protein). Such changes include, but are not limited to: changes in one or a few amino acid side chains; changes in one or a few amino acids, including deletions (e.g., a truncated version of the protein or peptide) insertions and/or substitutions; changes in stereochemistry of one or a few atoms; and/or minor derivatizations, including but not limited to: methylation, farnesylation, geranyl geranylation, glycosylation, carboxymethylation, phosphorylation, acetylation, myristoylation, prenylation, palmitation, and/or amidation. Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* 157:105 (1982)), or on the basis of the ability to assume similar polypeptide secondary structure (Chou and Fasman, *Adv. Enzymol.* 47: 45 (1978)).

A homologue can have enhanced, decreased, or substantially similar properties as compared to the naturally occurring protein or peptide. It is noted that homologues can include synthetically produced homologues, naturally occurring allelic variants of a given protein or domain, or homologous sequences from organisms other than the organism from which the reference sequence was derived. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications or mutations in protein homologues, as compared to the wild-type protein, increase, decrease, or do not substantially change, the basic biological activity of the homologue as compared to the naturally occurring (wild-type) protein. In general, the biological activity or biological action of a protein refers to any function(s) exhibited or performed by the protein that is ascribed to the naturally occurring form of the protein as measured or observed in vivo (i.e., in the natural environment of the protein) or in vitro (i.e., under laboratory conditions). Modifications of a protein, such as in a homologue, may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action (or activity) of a protein. Similarly, modifications which result in an increase in protein expression or an increase in the activity of the protein, can be referred to as amplification, overproduction, overexpression, activation, enhancement, up-regulation or increased action (or activity) of a protein. It is noted that general reference to a homologue having the biological activity of the wild-type protein does not necessarily mean that the homologue has identical biological activity as the wild-type protein, particularly with regard to the level of biological activity. Rather, a homologue can perform the same biological activity as the wild-type protein, but at a reduced or increased level of activity as compared to the wild-type protein.

One embodiment of the present invention relates to isolated nucleic acid molecules comprising, consisting essentially of, or consisting of nucleic acid sequences that encode any of the enzymes described herein, including a homologue or fragment of any of such enzymes, as well as nucleic acid sequences that are fully complementary thereto. In accordance with the present invention, an isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Preferably, an isolated nucleic acid molecule of the present invention is produced using recombinant DNA technology (e.g., polymerase chain reaction (PCR) amplification, cloning) or chemical synthesis.

A nucleic acid molecule homologue can be produced using a number of methods known to those skilled in the art (see, for example, Sambrook et al., *Molecular Cloning: A Laboratory Manual*, Cold Spring Harbor Labs Press (1989)). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

Another embodiment of the present invention includes a recombinant nucleic acid molecule comprising a recombinant vector and a nucleic acid sequence encoding a protein or peptide having at least one enzymatic activity useful for catalyzing the conversion of lignocellulosic material to fermentable sugars. According to the present invention, a recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid molecules of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant organism (e.g., a microbe or a plant). The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

Typically, a recombinant nucleic acid molecule includes at least one nucleic acid molecule of the present invention operatively linked to one or more expression control sequences. According to the present invention, the phrase "operatively linked" refers to linking a nucleic acid molecule to an expression control sequence (e.g., a transcription control sequence and/or a translation control sequence) in a manner such that the molecule can be expressed when transfected (i.e., transformed, transduced, transfected, conjugated or conduced) into a host cell. Transcription control sequences are sequences that control the initiation, elongation, or termination of transcription. Particularly important transcription control sequences are those that control transcription initiation, such as promoter, enhancer, operator and repressor sequences. Suitable transcription control sequences include any transcription control sequence that can function in a host cell or organism into which the recombinant nucleic acid molecule is to be introduced.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as filamentous fungi, bacteria and yeast, or into plant cells. In microbial and plant systems, the term "transformation" is used to describe an inherited change due to the acquisition of exogenous nucleic acids by the microorganism or plant and is essentially synonymous with the term "transfection." Transfection techniques include, but are not limited to, transformation, particle bombardment, diffusion, active transport, bath sonication, electroporation, microinjection, lipofection, adsorption, infection and protoplast fusion.

The multi-enzyme products, in some embodiments, comprise a biomass including microorganisms or a crude fermentation product of microorganisms. A crude fermentation product refers to the fermentation broth which has been separated from the microorganism biomass (by filtration, for example). Microorganisms used in the present invention are cultured in an appropriate fermentation medium. An appropriate, or effective, fermentation medium refers to any medium in which a microorganism of the present invention, including a genetically modified microorganism, when cultured, is capable of expressing enzymes useful in the present invention and/or of catalyzing the production of sugars from lignocellulosic biomass. Such a medium is typically an aqueous medium comprising assimilable carbon, nitrogen and phosphate sources. Such a medium can also include appropriate salts, minerals, metals and other nutrients. Microorganisms of the present invention can be cultured in conventional fermentation bioreactors. The microorganisms can be cultured by any fermentation process which includes, but is not limited to, batch, fed-batch, cell recycle, and continuous fermentation. The fermentation of microorganisms such as fungi may be carried out in any appropriate reactor, using methods known to those skilled in the art. For example, the fermentation may be carried out for a period of 1 to 14 days, or more preferably between about 3 and 10 days. The temperature of the medium is typically maintained between about 25 and 50° C., and more preferably between 28 and 40° C. The pH of the fermentation medium is regulated to a pH suitable for growth and protein production of the particular organism. The fermentor can be aerated in order to supply the oxygen necessary for fermentation and to avoid the excessive accumulation of carbon dioxide produced by fermentation. In addition, the aeration helps to control the temperature and the moisture of the culture medium. In general the fungal strains are grown in fermentors, optionally centrifuged or filtered to remove biomass, and optionally concentrated, formulated, and dried to produce a multi-enzyme product that is a crude fermentation product.

In other embodiments, the multi-enzyme products are subjected to one or more purification steps, such as ammonium sulfate precipitation, chromatography, and/or ultrafiltration. In other embodiments certain of the enzymes may be obtained from a commercial source.

In one embodiment, the invention provides a multi-enzyme product, or at least one enzyme derived from such a multi-enzyme product, comprising a product of a *Chrysosporium* including *Chrysosporium lucknowense* and exhibiting: a glucoamylase activity of at least about 0.05 U per milligram of dry matter, a β-glucosidase activity of at least about 22 nmol/min/mg of dry matter, and an α-arabinofuranosidase activity of at least about 9 nmol/min/mg of dry matter. In some embodiments, the Chrysosporium lucknowense may be Strain C1 Strain C1 (Accession No. VKM F-3500-D); Strain UV13-6 (Accession No. VKM F-3632 D); Strain NG7C-19 (Accession No. VKM F-3633 D); and/or Strain UV18-25 (Accession No. VKM F-3631 D) or a mutant or derivative thereof.

The activities of the *Chrysosporium* enzymes may be higher or lower than the values listed above. For example, the product may exhibit a glucoamylase activity of between about 0.01 and about 0.1 U per milligram of dry matter. In certain embodiments, the product may exhibit a glucoamylase activity of at least about 0.01, 0.025, 0.05 or 0.075 U per milligram of dry matter. The product may exhibit a β-glucosidase activity of between about 5 and about 50 nmol/min/mg of dry matter. In certain embodiments, the product may exhibit a β-glucosidase activity of at least about 5, 15, 22 or 30 nmol/min/mg of dry matter. The product may exhibit an α-arabinofuranosidase activity of between about 1 and about 20 nmol/min/mg of dry matter. In certain embodiments, the product may exhibit an α-arabinofuranosidase activity of at least about 1, 5, 9 or 15 nmol/min/mg of dry matter.

In one embodiment, the invention provides a multi-enzyme product, or at least one enzyme derived from such a multi-enzyme product, comprising a product of a *Trichoderma* including *Trichoderma reesei* and exhibiting: a glucoamylase activity of at least about 0.001 U per milligram of dry matter, a β-xylosidase activity of at least about 280 nmol/min/mg of dry matter, a β-glucosidase activity of at least about 454 nmol/min/mg of dry matter, and an α-arabinofuranosidase activity of at least about 100 nmol/min/mg of dry matter. In some embodiments, the *Trichoderma reesei* is ATCC strain QM6A or a derivative thereof.

The activities of the *Trichoderma* enzymes may be higher or lower than the values listed above. For example, the product may exhibit a glucoamylase activity of between about 0.0005 and about 0.005 U per milligram of dry matter. In certain embodiments, the product may exhibit a glucoamylase activity of at least about 0.0005, 0.00075, 0.001 or 0.0025 U per milligram of dry matter. The product may exhibit a β-xylosidase activity of between about 50 and about 500 nmol/min/mg of dry matter. In certain embodiments, the product may exhibit a β-xylosidase activity of at least about 50, 150, 250 or 350 nmol/min/mg of dry matter. The product may exhibit a β-glucosidase activity of between about 100 and about 1000 nmol/min/mg of dry matter. In certain embodiments, the product may exhibit β-glucosidase activity of at least about 100, 250, 400 or 600 nmol/min/mg of dry matter. The product may exhibit an α-arabinofuranosidase activity of between about 25 and about 200 nmol/min/mg of dry matter. In certain embodiments, the product may exhibit an α-arabinofuranosidase activity of at least about 25, 50, 75 or 150 nmol/min/mg of dry matter.

In one embodiment, the invention provides a multi-enzyme product, or at least one enzyme derived from such a multi-enzyme product, comprising a product of a *Aspergillus* including *Aspergillus japonicus* and exhibiting: a glucoamylase activity of at least about 0.65 U per milligram of dry matter, a β-xylosidase activity of at least about 553 nmol/min/mg of dry matter, a β-glucosidase activity of at least about 167 nmol/min/mg of dry matter, and an α-arabinofuranosidase activity of at least about 62 nmol/min/mg of dry matter.

The activities of the *Aspergillus* enzymes may be higher or lower than the values listed above. For example, the product may exhibit a glucoamylase activity of between about 0.15 and about 1.0 U per milligram of dry matter. In certain embodiments, the product may exhibit a glucoamylase activity of at least about 0.15, 0.30, 0.60 or 0.80 U per milligram of dry matter. The product may exhibit a β-xylosidase activity of between about 100 and about 1000 nmol/min/mg of dry matter. In certain embodiments, the product may exhibit a β-xylosidase activity of at least about 100, 250, 400 or 600 nmol/min/mg of dry matter. The product may exhibit a β-glucosidase activity of between about 40 and about 400 nmol/min/mg of dry matter. In certain embodiments, the product may exhibit a β-glucosidase activity of at least about 40, 100, 150 or 250 nmol/min/mg of dry matter. The product may exhibit an α-arabinofuranosidase activity of between about 15 and about 150 nmol/min/mg of dry matter. In certain embodiments, the product may exhibit an α-arabinofuranosidase activity of at least about 15, 30, 50 or 100 nmol/min/mg of dry matter.

In one embodiment, the invention provides a multi-enzyme product, or at least one enzyme derived from such a multi-enzyme product, comprising a product of a *Penicillium* including *Penicillium funiculosum* and exhibiting: a glucoamylase activity of at least about 0.18 U per milligram of dry matter, a β-xylosidase activity of at least about 8 nmol/min/mg of dry matter, a β-glucosidase activity of at least about 691 nmol/min/mg of dry matter, and an α-arabinofuranosidase activity of at least about 29 nmol/min/mg of dry matter.

The activities of the *Penicillium* including *Penicillium funiculosum* enzymes may be higher or lower than the values listed above. For example, the product may exhibit a glucoamylase activity of between about 0.04 and about 0.40 U per milligram of dry matter. In certain embodiments, the product may exhibit a glucoamylase activity of at least about 0.04, 0.1, 0.16 or 0.25 U per milligram of dry matter. The product may exhibit a β-xylosidase activity of between about 1 and about 20 nmol/min/mg of dry matter. In certain embodiments, the product may exhibit a β-xylosidase activity of at least about 1, 4, 8 or 15 nmol/min/mg of dry matter. The product may exhibit a β-glucosidase activity of between about 150 and about 1500 nmol/min/mg of dry matter. In certain embodiments, the product may exhibit a β-glucosidase activity of at least about 150, 300, 600 or 1000 nmol/min/mg of dry matter. The product may exhibit an α-arabinofuranosidase activity of between about 5 and about 50 nmol/min/mg of dry matter. In certain embodiments, the product may exhibit an α-arabinofuranosidase activity of at least about 5, 15, 25 or 40 nmol/min/mg of dry matter.

In one embodiment, the invention provides a multi-enzyme product, or at least one enzyme derived from such a multi-enzyme product, comprising a product of a *Penicillium canescens* and exhibiting: a glucoamylase activity of at least about 0.08 U per milligram of dry matter, a β-xylosidase activity of at least about 15 nmol/min/mg of dry matter, a β-glucosidase activity of at least about 40 nmol/min/mg of dry matter, and an α-arabinofuranosidase activity of at least about 956 nmol/min/mg of dry matter.

The activities of the *Penicillium canescens* enzymes may be higher or lower than the values listed above. For example, the product may exhibit a glucoamylase activity of between about 0.01 and about 0.2 U per milligram of dry matter. In certain embodiments, the product may exhibit a glucoamylase activity of at least about 0.01, 0.04, 0.08 or 0.12 U per milligram of dry matter. The product may exhibit a β-xylosidase activity of between about 4 and about 40 nmol/min/mg of dry matter. In certain embodiments, the product may exhibit a β-xylosidase activity of at least about 4, 8, 15 or 25 nmol/min/mg of dry matter. The product may exhibit a 0-glucosidase activity of between about 10 and about 100 nmol/min/mg of dry matter. In certain embodiments, the product may exhibit a β-glucosidase activity of at least about 10, 20, 35 or 60 nmol/min/mg of dry matter. The product may exhibit an α-arabinofuranosidase activity of between about 200 and about 2000 nmol/min/mg of dry matter. In certain embodiments, the product may exhibit an α-arabinofuranosidase activity of at least about 200, 400, 800 or 1250 nmol/min/mg of dry matter.

In one embodiment, the invention provides any combination of any one or more enzymes derived from any one or more of the multi-enzyme products described above. Such enzymes can be isolated from the microorganism described above (e.g., as a crude fermentation product, partially purified enzyme, or purified enzyme) or can be produced recombinantly from the knowledge of the structure of such enzyme. Homologues of any of such enzymes are also included for use in the present invention.

In one embodiment, the invention provides a multi-enzyme product comprising an Aspergillus β-xylosidase, a *Penicillium* or *Talaromyces* β-glucosidase, and a *Penicillium* α-arabinofuranosidase. In one embodiment, the invention provides a multi-enzyme product comprising an *Aspergillus japonicus* β-xylosidase, a *Penicillium funiculosum* β-glucosidase, and a *Penicillium canescens* α-arabinofuranosidase.

In one embodiment, the invention provides a multi-enzyme product comprising a *Chrysosporium lucknowense* β-glucosidase, such as the enzyme described in U.S. Pat. No. 6,015,707, incorporated herein by reference in its entirety.

In some embodiments, the multi-enzyme products comprise an accessory enzyme. An accessory enzyme is an additional enzyme capable of hydrolyzing lignocellulose. These enzymes have been described elsewhere herein, and can generally include cellulases, xylanases, ligninases, amylases, proteases, lipidases, glucuronidases, for example. This can include enzymes that when contacted with biomass in a reaction, allow for an increase in the activity of enzymes (e.g. hemicellulases) in the multi-enzyme product. It is understood that many classes of enzymes may function as accessory enzymes, in particular accessory enzymes can be composed of (but not limited to) enzymes of the following classes: cellulases, xylanases, ligninases, amylases, proteases, lipidases and glucuronidases. An accessory enzyme or enzyme mix may be composed of enzymes from (1) commercial suppliers; (2) cloned genes expressing enzymes; (3) complex broth (such as that resulting from growth of a microbial strain in media, wherein the strains secrete proteins and enzymes into the media); (4) cell lysates of strains grown as in (3); and, (5) plant material expressing enzymes capable of degrading lignocellulose. In some embodiments, the accessory enzyme is a glucoamylase, a pectinase, or a ligninase.

As used herein, a ligninase is an enzyme that can hydrolyze or break down the structure of lignin polymers, including lignin peroxidases, manganese peroxidases, laccases, and other enzymes described in the art known to depolymerize or otherwise break lignin polymers. Also included are enzymes capable of hydrolyzing bonds formed between hemicellulosic sugars (notably arabinose) and lignin.

The present invention is also drawn to several methods for hydrolyzing lignocellulose and the generation of fermentable sugars therefrom. In one embodiment, the method comprises contacting the lignocellulosic material with an effective amount of a multi-enzyme product derived from one or more microorganisms, whereby at least one fermentable sugar is produced (liberated). The lignocellulosic material may be partially or completely degraded to fermentable sugars. Economical levels of degradation at commercially viable costs are contemplated. Examples of enzymes contained in multi-enzyme products are described elsewhere herein. The microorganism can be any microorganism as described above, including a genetically modified microorganism. In one embodiment, the microorganism a filamentous fungus. In a further embodiment, the multi-enzyme product comprises at least one enzyme including a combination of enzymes from a fungus from the genus *Talaromyces, Trichoderma, Chrysosporium, Aspergillus*, or *Penicillium*. In a further embodiment, the multi-enzyme product comprises at least one enzyme including a combination of enzymes that is derived from *Trichoderma reesei, Chrysosporium lucknowense, Aspergillus japonicus, Penicillium canescens, Penicillium funiculosum*, or mutants of any of the foregoing. In yet another embodiment, the multi-enzyme product comprises at least one enzyme including a combination of enzymes from Strain C1 (Accession No. VKM F-3500-D); Strain UV13-6 (Accession No. VKM F-3632 D); Strain NG7C-19 (Accession No. VKM F-3633 D); and/or Strain UV18-25 (Accession No. VKM F-3631 D) or mutants or derivatives thereof. Examples of these multi-enzyme products are described above.

An effective amount of a multi-enzyme product derived from one or more microorganisms is an amount that at least partially degrades a lignocellulosic material to fermentable sugars. Effective amounts vary with the activity of each enzyme in the multi-enzyme product, as described above. Typically, an enzyme or a multi-enzyme product is used in an amount of between about 0.02% and about 0.2% by weight of the lignocellulosic material. In some embodiments, the enzyme or multi-enzyme product is used in an amount of at least about 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19% or 0.2% by weight of the lignocellulosic material.

In some embodiments, the enzyme or multi-enzyme product is used in an amount of between about 0.1 mg and about 60 mg per gram of dry biomass. In certain embodiments, the enzyme or multi-enzyme product is used in an amount of about 0.1, 0.5, 1.0, 5, 10, 15, 20, 25, 30, 35, 40, 45, 50, 55 or 60 mg per gram of dry biomass.

In a further embodiment, the invention provides a method for degrading DDG (or DDGS), preferably derived from corn, to sugars. The method comprises contacting the DDG with a multi-enzyme product obtained from the fermentation of at least one microorganism. Such multi-enzyme products are described elsewhere herein. In this embodiment, at least 10% of said fermentable sugars are liberated. At least one of the enzymes in the multi-enzyme product is selected from the group consisting of at least one enzyme in the multi-enzyme products of *Trichoderma* including *Trichoderma reesei, Chrysosporium* including *Chrysosporium lucknowense*, (including Strain C1 (Accession No. VKM F-3500-D); Strain UV13-6 (Accession No. VKM F-3632 D); Strain NG7C-19 (Accession No. VKM F-3633 D); and/or Strain UV18-25 (Accession No. VKM F-3631 D)), *Aspergillus* including *Aspergillus japonicus, Penicillium* including *Penicillium canescens* or *solitum, Penicillium* including *Penicillium funiculosum* (*Talaromyces* including *Talaromyces flavus*), or mutants thereof as described herein. In other embodiment, the at least 15% of the sugars are liberated, or at least 20% of the sugars are liberated, or at least 23% of the sugars are liberated, or at least 24% of the sugars are liberated, or at least 25% of the sugars are liberated, or at least 26% of the sugars are liberated, or at least 27% of the sugars are liberated, or at least 28% of the sugars are liberated.

In a further embodiment, the invention provides a method for producing fermentable sugars comprising cultivating a microorganism, such as *Trichoderma* including *Trichoderma reesei, Chrysosporium* including *Chrysosporium lucknowense, Aspergillus* including *Aspergillus japonicus, Penicillium* including *Penicillium canescens* or *solitum, Penicillium* including *Penicillium funiculosum* (*Talaromyces* including *Talaromyces flavus*) or mutants thereof in a nutrient medium comprising a lignocellulosic material, whereby fermentable sugars are produced.

Also provided are methods that comprise further contacting the lignocellulosic material with at least one accessory enzyme. Accessory enzymes have been described elsewhere herein. The accessory enzyme or enzymes may be added at the same time, prior to, or following the addition of the multi-enzyme product, or can be expressed (endogenously or overexpressed) in a genetically modified microorganism used in a method of the invention. When added simultaneously, the multi-enzyme product will be compatible with the accessory enzymes selected. When the enzymes are added following the treatment with the multi-enzyme product, the conditions (such as temperature and pH) may be altered to those optimal for the accessory enzyme before, during, or after addition of the accessory enzyme. Multiple rounds of multi-enzyme product and accessory enzyme addition are also encompassed. The accessory enzyme may also be present in the lignocellulosic material itself as a result of genetically modifying the plant. The nutrient medium used in a fermentation can also comprise one or more accessory enzymes.

In some embodiments, the method comprises a pretreatment process. In general, a pretreatment process will result in components of the lignocellulose being more accessible for downstream applications or so that it is more digestible by enzymes following treatment in the absence of hydrolysis. The pretreatment can be a chemical, physical or biological pretreatment. The lignocellulose may have been previously treated to release some or all of the sugars, as in the case of DDG. Physical treatments, such as grinding, boiling, freezing, milling, vacuum infiltration, and the like may also be used with the methods of the invention. In one embodiment, the heat treatment comprises heating the lignocellulosic material to at least about 121° C. for at least about 15 minutes. A physical treatment such as milling can allow a higher concentration of lignocellulose to be used in the methods of the invention. A higher concentration refers to about 20%, up to about 25%, up to about 30%, up to about 35%, up to about 40%, up to about 45%, or up to about 50% lignocellulose. The lignocellulose may also be contacted with a metal ion, ultraviolet light, ozone, and the like. Additional pretreatment processes are known to those skilled in the art, and can include, for example, organosolv treatment, steam explosion treatment, lime impregnation with steam explosion treatment, hydrogen peroxide treatment, hydrogen peroxide/ozone (peroxone) treatment, acid treatment, dilute acid treatment, and base treatment, including ammonia fiber explosion (AFEX) technology. Details on pretreatment technologies and processes can be found in Wyman et al., *Bioresource Tech.* 96:1959 (2005); Wyman et al., *Bioresource Tech.* 96:2026 (2005); Hsu, "Pretreatment of biomass" In Handbook on Bioethanol: Production and Utilization, Wyman, Taylor and Francis Eds., p. 179-212 (1996); and Mosier et al., *Bioresource Tech.* 96:673 (2005).

In an additional embodiment, the method comprising detoxifying the lignocellulosic material. Dextoxification may be desirable in the event that inhibitors are present in the lignocellulosic material. Such inhibitors can be generated by a pretreatment process, deriving from sugar degradation or are direct released from the lignocellulose polymer. Detoxifying can include the reduction of their formation by adjusting sugar extraction conditions; the use of inhibitor-tolerant or inhibitor-degrading strains of microorganisms. Detoxifying can also be accomplished by the addition of ion exchange resins, active charcoal, enzymatic detoxification using, e.g., laccase, and the like. In some embodiments, the multi-enzyme products (such as those derived from *T. reesei*, for example) comprise detoxifying agents.

In some embodiments, the methods may be performed one or more times in whole or in part. That is, one may perform one or more pretreatments, followed by one or reactions with a multi-enzyme product and/or accessory enzyme. The enzymes may be added in a single dose, or may be added in a series of small doses. Further, the entire process may be repeated one or more times as necessary. Therefore, one or more additional treatments with heat and enzymes are contemplated.

The methods result in the production of fermentable sugars. During, or subsequent to the methods described, the fermentable sugars may be recovered. In the case of a cultivation of microorganisms, the sugars can be recovered through a continuous, batch or fed-batch method. The sugars recovered can be concentrated or purified. Recovery may occur by any method known in the art, including, but not limited to, washing, gravity flow, pressure, chromatography, extraction, crystallization (e.g., evaporative crystallization), membrane separation, reverse osmosis, distillation, and filtration. The sugars can be subjected further processing; e.g., they can also be sterilized, for example, by filtration.

In a related embodiment, the invention provides means for improving quality of lignocellulosic material, including DDG and DDGS for animal nutrition. In one embodiment, the residual lignocellulosic material (e.g., a lignocellulosic material which has been saccharified) is recovered (e.g., has the soluble sugars removed). The recovered material can be used as an animal feed additive. It is believed that the recovered material will have beneficial properties for animal nutrition, such as, for example, a higher protein content, higher protein quality, improved palatability, improved digestibility, improved nutritional value. The feed additive (or feeds containing the additive) may be administered to animals to improve the performance of the animal. In some embodiments, administering the feed additive to an animal may result in increased animal growth or physiological performance.

In an additional embodiment, the invention provides a method for producing an organic substance, comprising saccharifying a lignocellulosic material with an effective amount of a multi-enzyme product obtained from at least one microorganism as in any of the methods described herein, fermenting the saccharified lignocellulosic material obtained with one or more fermenting microorganisms, and recovering the organic substance from the fermentation. Sugars released from biomass can be converted to useful fermentation products including but not limited to amino acids, vitamins, pharmaceuticals, animal feed supplements, specialty chemicals, chemical feedstocks, plastics, solvents, fuels, or other organic polymers, lactic acid, and ethanol, including fuel ethanol. Specific products that may be produced by the methods of the invention include, but not limited to, biofuels (including ethanol); lactic acid; plastics; specialty chemicals; organic acids, including citric acid, succinic acid and maleic acid; solvents; animal feed supplements; pharmaceuticals; vitamins; amino acids, such as lysine, methionine, tryptophan, threonine, and aspartic acid; industrial enzymes, such as proteases, cellulases, amylases, glucanases, lactases, lipases, lyases, oxidoreductases, and transferases; and chemical feedstocks. The methods of the invention are also useful to generate feedstocks for fermentation by fermenting microorganisms. In one embodiment, the method further comprises the addition of at least one fermenting organism. As used herein, "fermenting organism" refers to an organism capable of fermentation, such as bacteria and fungi, including yeast. Such feedstocks have additional nutritive value above the nutritive value provided by the liberated sugars.

Additional objects, advantages, and novel features of this invention will become apparent to those skilled in the art upon examination of the following examples thereof, which are not intended to be limiting.

EXAMPLES

Example 1

Hydrolysis of DDG with Enzyme Complexes from Fungal Strains

DDG was washed twice with water and dried to remove most of the soluble starch, glucose and glycerol that could cause erroneously high readings of reducing sugar released by the enzymes acting on the polysaccharides in the DDG.

Specific test conditions for the experiment were:
125 ml erlenmeyer flask
40 ml total volume
10% w/w washed DDG
Temperature=50° C.
25 mM sodium acetate, pH 5.0
0.02% sodium azide as preservative
Total enzyme loading: 0.2% w/w of DDG loading (20 mg of dry enzyme preparation per 10 g dry DDG)
Agitated in incubator/shaker at 150 rpm
Sampled at 0, 24, 48 and 72 hours
Samples were centrifuged, supernatants separated and filtered, then heat treated at 80° C. for 20 minutes to inactivate enzymes and stop further hydrolysis of oligosaccharides.

The enzymes samples used were dried fermentation samples of commercial and experimental fungal strains. The specific fungal species tested were *Chrysosporium lucknowense, Trichoderma reesei, Aspergillus japonicus, Penicillium funiculosum*, and *Penicillium canescens*.

Figure 1:
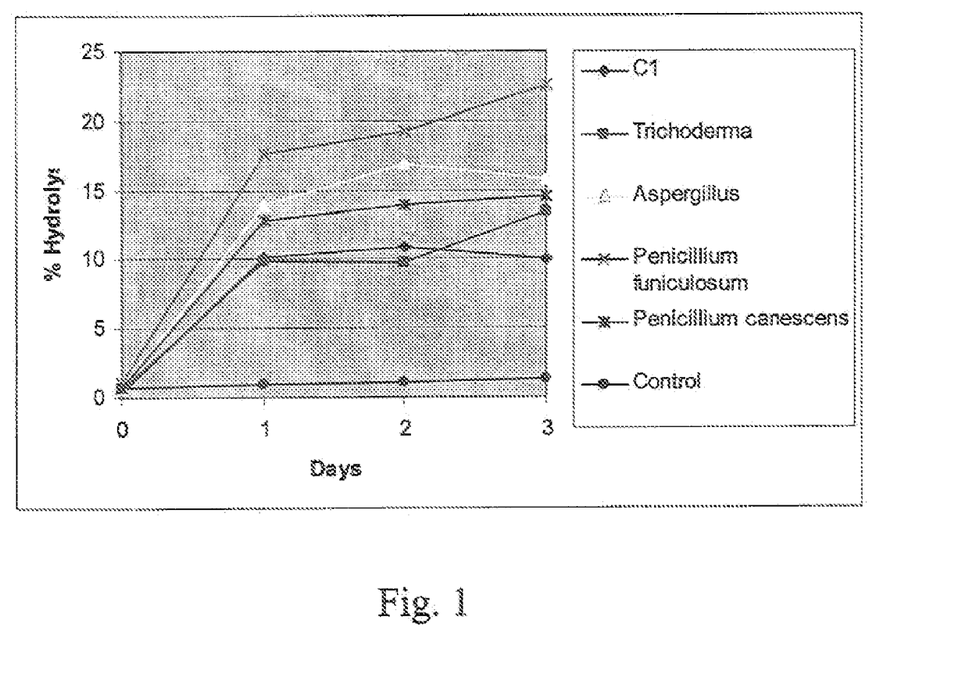
FIG. 1 shows hydrolysis of DDG with enzyme complexes from fungal strains over time.

Duplicate flasks of each condition were prepared. Reducing sugars released into the supernatant were measured using the dinitrosalicylic acid (DNS) assay. The average values from the duplicate flasks are shown in FIG. 1. The data are presented as percent hydrolysis of DDG based on a theoretical maximum of 400 mM (100% degradation), which was estimated as follows. The composition of DDG is approximately 32% hemicellulose, 22% cellulose, and 4% starch. Thus, about 58% of the dry weight of DDG is polysaccharides with somewhat over half of that contributed by hemicellulose. Therefore, a starting concentration of 10% w/w DDG implies there will be approximately 3.2% (0.24 M) pentoses and 2.6% (0.16 M) glucose=0.4 M total reducing sugars. This composition undoubtedly varies depending on the source of the corn, time and conditions of storage of the corn, dry mill ethanol plant, batch of corn grind, temperature of liquefaction and saccharification step, quality of starch degrading enzymes and length of incubation, and the particular yeast fermentation. The conditions downstream from the corn grind probably have the greatest impact on the residual starch and glucose content.

The results indicated that all of the enzymes tested hydrolyze DDG. The *Penicillium funiculosum* strain was the most effective at hydrolysis. Under the conditions tested, approximately 23% of the total theoretical hydrolysis occurred with this strain after 72 hours.

Example 2

Products of Enzymatic Hydrolysis of DDG

The 72 hour samples from Example 1 were analyzed by HPLC with refractive index detection to determine the identity and concentration of monomeric sugars in solution. Table 1 summarizes the results. The best overall total sugar monomer release was observed with the *Penicillium funiculosum* sample. The principal arabinoxylan component sugars, L-arabinose and D-xylose are highest in the *Penicillium canescens* preparation.

TABLE 1

Monomeric sugars released after hydrolysis of DDG with fungal enzymes.

| Sample | Trichoderma reesei | Chrysosporium lucknowense | Aspergillus japonicus | Penicillium canescens | Penicillium funiculosum | Control |
|---|---|---|---|---|---|---|
| Glucose (mM) | 25.8 | 22.6 | 50.9 | 28.2 | 58.2 | 0.3 |
| Xylose (mM) | 6.1 | 3.9 | 9.1 | 14.3 | 9.2 | 0.2 |
| Arabinose (mM) | 6.1 | 8.2 | 9.7 | 18.7 | 13.8 | 1.0 |
| Glc + Xyl + Ara (mM) | 38.0 | 34.6 | 69.6 | 61.2 | 81.2 | 1.5 |

Glycosidase enzyme activities were determined for the fungal enzyme samples using the appropriate p-nitrophenyl glycoside substrates. Results are shown in Table 2.

TABLE 2

Glycosidase activities in fungal enzyme complexes.

| | Enzyme Activities | | |
|---|---|---|---|
| Enzyme Sample | β-xylosidase nmol/min/mg solids | β-glucosidase nmol/min/mg solids | α-arabinofuranosidase nmol/min/mg solids |
| Trichoderma reesei | 280 | 454 | 100 |
| Chrysosporium lucknowense | 0 | 22 | 9 |
| Aspergillus japonicus | 553 | 167 | 62 |
| Penicillium canescens | 15 | 40 | 956 |
| Penicillium funiculosum | 8 | 691 | 29 |

There is some correlation between the preparations with the highest α-arabinofuranosidase activity and arabinose released. The highest level of arabinose observed is in samples hydrolyzed with the *Penicillium canescens* enzyme complex, which also has the highest α-arabinofuranosidase activity. There is no readily apparent correlation between β-xylosidase activity and xylose released. The highest xylose release is also seen with Penicillium canescens, which has very low β-xylosidase activity. However, it is possible that the α-arabinofuranosidase activity of this preparation, by releasing arabinose, makes the xylan backbone of the hemicellulose more accessible to xylanases in this strain. There is some correlation between β-glucosidase activity and glucose released. The highest levels of glucose are observed in the *Penicillium funiculosum* strain, which also has the highest level of this enzyme. The *Aspergillus japonicus* preparation also shows high levels of glucose release, even though the β-glucosidase activity is relatively low. This could possibly be due to amylase activity releasing glucose from the residual starch. The glucoamylase specific activities of these strains are indicated in Table 3. The three enzyme activities of Table 2 were measured with the artificial p-nitrophenyl-glycoside substrate whereas the enzymes encounter very different natural substrates in the DDG. These natural substrates may be hydrolyzed better than the artificial substrate by the particular glycosidase found in a given organism. Also, there are likely to be synergies between different enzymes in effecting hydrolysis of arabinoxylan. There appears to be a correlation between high α-arabinofuranosidase activity and the release of both arabinose and xylose, possibly due to the removal of the arabinose side chains from the xylan backbone, thus creating a better substrate for both xylanase and β-xylosidase, as noted above.

TABLE 3

Glucoamylase specific activity of fungal strains

| Strain | Glucoamylase specific activity, U/mg protein |
| --- | --- |
| *Trichoderma reesei* | 0.001 |
| *Chrysosporium lucknowense* | 0.05 |
| *Aspergillus japonicus* | 0.65 |
| *Penicillium canescens* | 0.08 |
| *Penicillium funiculosum* | 0.18 |

Example 3

Enzyme complexes from Different Fungi Act Synergistically on Untreated and Heat-Treated DDG Test conditions were similar to those used in Example 2 except for the addition of magnesium and calcium cations in the event that the glycosidases needed one of these divalent cations for full activity or extended stability (lifetime).
  125 ml Erlenmeyer flask
  40 ml total volume
  10% w/w washed DDG
  Temperature=50° C.
  25 mM sodium acetate, pH 5.0
  1 mM MgCl$_2$ and 1 mM CaCl$_2$
  0.02% sodium azide as preservative
  Total enzyme loading: 0.2% w/w of DDG loading (20 mg of a binary (1:1) enzyme mixture per 10 g dry DDG=10 mg of each enzyme preparation per 10 g dry DDG).
  Agitated in incubator/shaker at 150 rpm
  Second enzyme loading at 24 hours at 0.1% w/w
  Sampled at 24, and 48 hours; controls also sampled at 0 hours.
  Samples were centrifuged, supernatants separated and filtered, then heat treated at 80° C. for 20 minutes to inactivate enzymes and stop further hydrolysis of oligosaccharides The enzymes used were those from *Aspergillus japonicus, Penicillium canescens*, and *Penicillium funiculosum*. Also, the following mixtures were used: (i) *Aspergillus japonicus* and *Penicillium canescens*; and (ii) *Penicillium canescens* and *Penicillium funiculosum*. When mixtures were used, the amount of each was half that used when single enzymes were used, i.e. the total weight of enzyme used in each incubation was the same.

Figure 2:
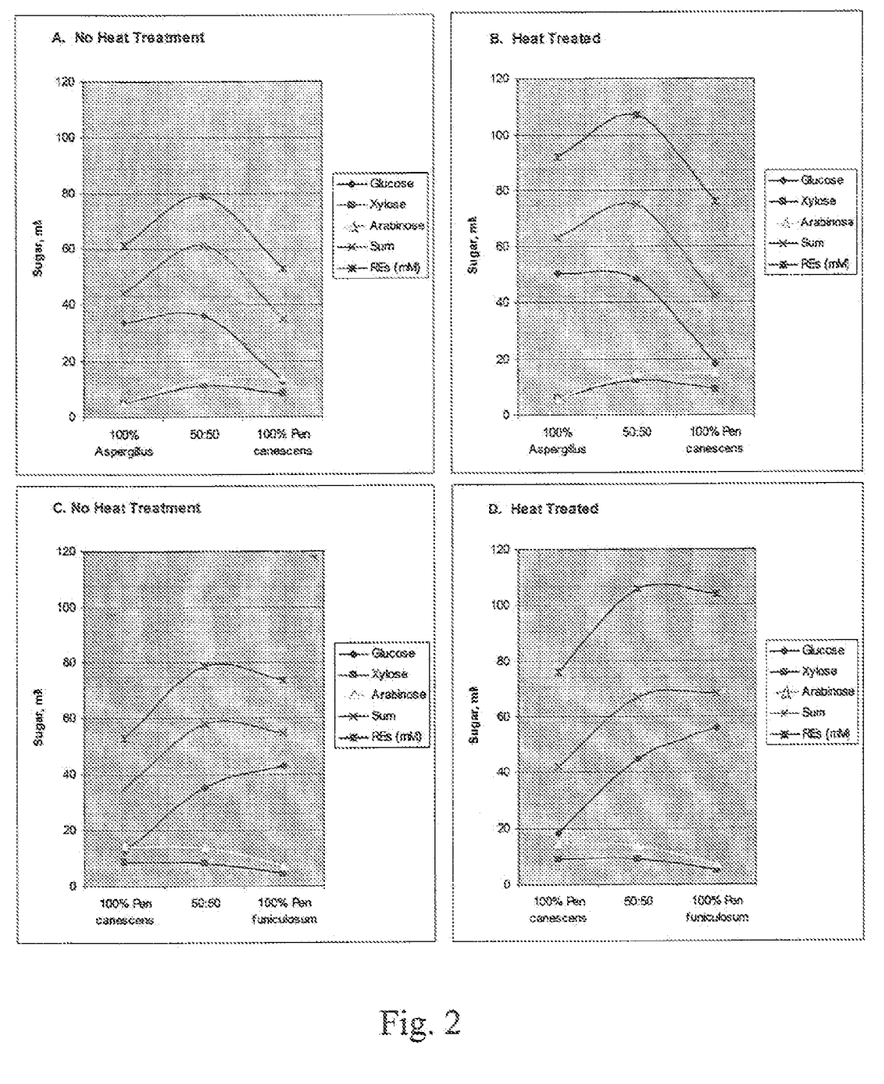
FIG. 2 shows the amount of sugar produced by enzymes and enzyme mixtures with untreated and heat-treated DDG. Synergism was found with certain enzyme mixtures. REs refers to reducing equivalents, a measure of number of cleavages in the sugar polymer.

FIG. 2 shows that when mixtures of enzymes are used and the total weight of the enzymes is held constant, the extent of total hydrolysis is greater with the mixture than with either of the individual enzymes in the mix. The sum of the monomers glucose, arabinose, and xylose and the total reducing sugars is highest with the 50:50 mixtures. While the synergism is less apparent when individual sugar yields are examined, the data suggest that complementarities of activities in the enzyme complexes results in increased total sugar release and increased hydrolytic activity in mixtures as compared with complexes from individual fungi.

The data also indicate that heat treatment by autoclaving at 121° C. for 15 minutes prior to enzyme hydrolysis is beneficial. Such treatment may expand the fibers, rendering them more accessible to enzymes.

Example 4

Addition of Glucoamylase Results in Increased Hydrolysis of DDG

Figure 3:
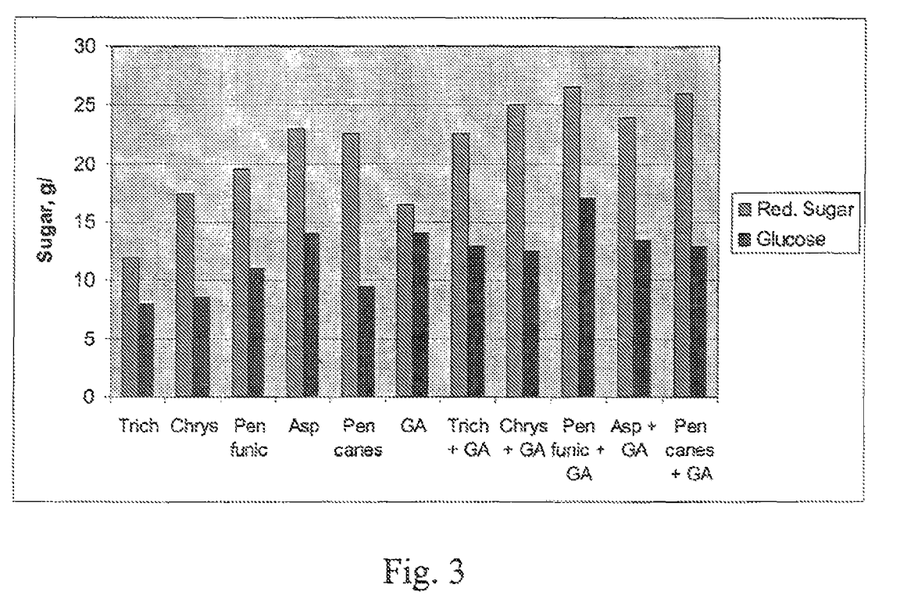
FIG. 3 shows glucose and reducing sugar yields after hydrolysis of DDG with fungal enzyme complexes with and without added glucoamylase.

In this experiment, DDG and enzymes were incubated in 10-mL tubes with magnetic stirring. Specific conditions were:
  1) 10% washed DDG
  2) Temperature=50° C.
  3) 50 mM sodium acetate, pH 5.0
  The preparations were normalized by protein (0.5 g/L total protein in the reaction mixture). To test the effect of glucoamylase (GA), a commercial glucoamylase product, Glucostar 400L (Dyadic International) was added to some of the mixtures. The ratio of enzyme complex to glucoamylase was 4:1, i.e. 0.4 g/L enzyme complex +0.1 g/L Glucostar 400L were used. The yields of reducing sugars after 48 hr DDG hydrolysis are shown in FIG. 3. In every case, addition of glucoamylase resulted in increased reducing sugar yields, indicating the presence of hydrolysable residual starch in DDG. Yields of glucose were also higher after addition of GA to all enzymes except for the *Aspergillus japonicus* complex, consistent with the already high amylase activity in this strain.

The presence of residual starch in DDG was demonstrated by reaction of DDG, before and after enzymatic hydrolysis, with iodine. This reaction is specific for starch resulting in blue color. The initial DDG gave an intense blue color with iodine, confirming the fact that the DDG contained residual starch. Samples of DDG after 48 hr hydrolysis under the action of some individual multienzyme preparations from *Trichoderma reesei, Chrysosporium lucknowense, Penicillium funiculosum*, and *Penicillium canescens* gave less intense blue color showing that most of the residual starch in DDG was destroyed. DDG hydrolyzed by *Aspergillus japonicus* showed no reaction with iodine, indicating that the starch had been completely hydrolyzed by this enzyme complex. Hydrolysis of DDG with Glucostar 400L alone and in combination with other preparations showed no reaction with iodine, indicating that the increased glucose and reducing sugar yields were at least partially attributable to hydrolysis of residual starch by GA.

Example 5

New Microbial Sources of Highly Efficient Hydrolytic Enzymes for Cellulosic Ethanol Production In the bioenergy field, the hydrolytic efficiency and cost of enzymes are the major limits to economical industrial bioethanol production. In order to address this issue, the inventors screened various fungal strains for effective saccharification of cellulosic biomass into fermentable sugars. Amorphous and purified cellulases and hemicellulases from a variety of native and recombinant fungi were evaluated at similar FPU. Saccharification was carried out using several hardwood and softwood substrates, pretreated by either organosolv or steam explosion processes. Results indicated that specific saccharification activity was significantly higher on organosolv pretreated wood than steam exploded wood. In addition the inventors were able to confirm that β-glucosidase helps to improve enzyme efficiency by preventing cellobiose end product inhibition. The presence of phenolic species generated during the steam explosion process may result in a toxic-inhibitory effect that might hinder saccharification. In this regard, the inventors were able to find that enzyme complexes from one fungal species appeared to be more stable in the presence of phenolic species. The results indicate that the hydrolytic efficiency of amorphous enzyme mixtures on pretreated lignocellulosic materials heavily depends on the sensitivities of individual enzymes to products, substrates, and toxic phenolics and on their optimal ratios within multienzyme complexes.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A multi-enzyme product comprising isolated enzymes from a *Trichoderma* and exhibiting: a glucoamylase activity of at least about 0.001 U per milligram of dry matter, a β-xylosidase activity of at least about 280 nmol/min/mg of dry matter, a β-glucosidase activity of at least about 454 nmol/min/mg of dry matter, and an α-arabinofuranosidase activity of at least about 100 nmol/min/mg of dry matter, wherein the multi-enzyme product increases the yield of fermentable sugars from Distiller's Dried Grains (DDG) over compositions not including the claimed amount of glucoamylase.

2. The multi-enzyme product of claim 1, wherein the product is a crude fermentation product.

3. The multi-enzyme product of claim 1, wherein the product has been subjected to a purification step.

4. The multi-enzyme product of claim 1, wherein the *Trichoderma* is *Trichoderma reesei*.

5. The multi-enzyme product of claim 1, wherein the product is capable of converting lignocellulosic material to sugars.

6. The multi-enzyme product of claim 1, wherein the fermentable sugars comprise glucose.

7. The multi-enzyme product of claim 1, wherein the DDG is derived from corn.

* * * * *